United States Patent [19]

Siegemund et al.

[11] Patent Number: 5,684,193
[45] Date of Patent: Nov. 4, 1997

[54] PROCESS FOR THE PREPARATION OF PERFLUOROPROPIONYL FLUORIDE

[75] Inventors: Günter Siegemund, Hofheim; Raimund Franz, Kelkheim, both of Germany

[73] Assignee: Hoechst Aktiengesellschaft, Germany

[21] Appl. No.: 745,816

[22] Filed: Nov. 12, 1996

[30] Foreign Application Priority Data

Nov. 13, 1995 [DE] Germany .................. 195 42 190.6

[51] Int. Cl.[6] .................................................. C07C 51/58
[52] U.S. Cl. ........................................................ 562/851
[58] Field of Search ............................................ 562/851

[56] References Cited

U.S. PATENT DOCUMENTS

| | | |
|---|---|---|
| 3,321,515 | 5/1967 | Moore et al. . |
| 4,874,557 | 10/1989 | Kruse et al. ............................. 562/851 |
| 4,973,748 | 11/1990 | Strutz ...................................... 562/851 |
| 4,973,749 | 11/1990 | Siegemund et al. .................... 562/851 |

FOREIGN PATENT DOCUMENTS

| | | |
|---|---|---|
| 1468775 | 3/1969 | Germany . |
| 3901000 | 7/1990 | Germany . |
| 4-134064 | 5/1992 | Japan . |
| 1295174 | 11/1972 | United Kingdom . |

OTHER PUBLICATIONS

Aranda, G., et al, *Bull. Soc. Chim. France*:1890–1892 (1965).
Franz, R., *J. Fluorine Chem.* 15:423–434 (1980).
Bull. Soc. Chim, France, 1965, pp. 1890–1892, XP000618042.

Primary Examiner—Paul J. Killos
Attorney, Agent, or Firm—Connolly & Hutz

[57] ABSTRACT

The invention relates to a process for the preparation of perfluoropropionyl fluoride (II) by the isomerization of hexafluoropropene oxide (I):

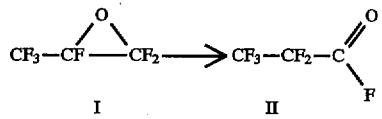

wherein the reaction medium used is a liquid complex ammonium hydrofluoride.

10 Claims, No Drawings

PROCESS FOR THE PREPARATION OF PERFLUOROPROPIONYL FLUORIDE

The present invention relates to a process for the selective preparation of perfluoropropionyl fluoride (II) by the isomerization of hexafluoropropene oxide (I):

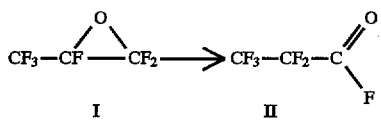

Hexafluoropropene oxide (I) and perfluoropropionyl fluoride (II) are the starting materials for the preparation of perfluoro(n-propyl vinyl ether), PPVE, a valuable comonomer for the production of modified polytetrafluoroethylene. PPVE is prepared according to the following scheme:

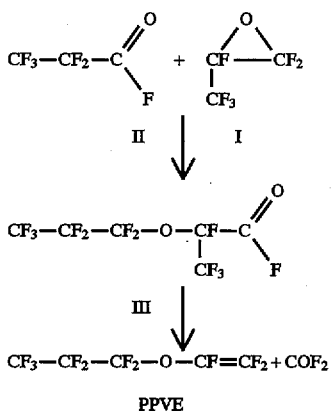

PPVE

Hexafluoropropene oxide (I) can thus be attacked by its own isomerization product (II) to form an ether-carboxylic acid fluoride (III). Analogously to the reaction of (II) with (I), however, it is also possible for (III) to react further with (I) to give a higher ether-carboxylic acid fluoride, which in turn reacts with (I), ultimately forming perfluorinated polyether-carboxylic acid fluorides. The known processes for the isomerization of hexafluoropropene oxide (I) to perfluoropropionyl fluoride (II) therefore have considerable disadvantages as regards the selectivity or the reaction times.

Thus, for example, U.S. Pat. No. 3,321,515 describes the isomerization of perfluorinated epoxides, which produces perfluorinated ketones in the presence of catalytic amounts of Lewis acids, but produces the corresponding acid fluorides in the presence of catalytic amounts of Lewis bases. The Lewis acids used are acidic metal oxides and metal halides; on the other hand, the Lewis bases used are fluorine ions in the form of alkali metal fluorides or compounds capable of producing fluorine ions in the reaction medium, e.g. tertiary amines (including pyridine), N-oxides thereof and tertiary acid amides. A number of examples in the said patent describe the isomerization of hexafluoropropene oxide (I) (HFPO) with basic catalysts to give perfluoropropionyl fluoride (II). This always involves the application of high pressures or very long reaction times, or both. In principle, therefore, the reactions must be carried out in pressure vessels and the formation of an oily by-product is often mentioned. Directly added fluoride is clearly rather unsuitable as the catalyst (Table II, Ex. Method 9 and 25), while amines (producing fluoride ions) give somewhat better results in some cases (Ex. Method 16, 20, 21, 33, 36, 38, 56). However, none of the catalysts described in U.S. Pat. No. 3,321,515 effects a rapid and simultaneously pressureless isomerization of hexafluoropropene oxide (I) to perfluoropropionyl fluoride (II) with high yields, as would be desirable for these two low-boiling substances.

Again, according to Japanese patent 04 134 046, published much later in 1990, which likewise describes the isomerization of hexafluoropropene oxide (I) to perfluoropropionyl fluoride (II) in the presence of tertiary amines, pyridines and quinolines, the carboxylic acid fluoride is obtained after a reaction time of 4 h with a yield of only 61.9% of theory. It is therefore obviously very difficult to prevent the perfluoropropionyl fluoride (II), formed by isomerization, from reacting further with hexafluoropropene oxide (I). This further reaction has even been utilized specifically for the preparation of mixtures of perfluorinated polyether-carboxylic acid fluorides. Thus, according to DE-A-3 901 000, a mixture of oligomeric ether-carboxylic acid fluorides of the general formula

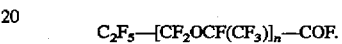

is obtained from hexafluoropropene oxide (I) in an aprotic solvent in the presence of tetramethylethylenediamine.

Against the background of this state of the art, it was very surprising to find that hexafluoropropene oxide (I) is selectively isomerized to perfluoropropionyl fluoride (II) under very mild conditions when a liquid complex ammonium hydrofluoride of the general formula (III):

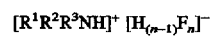

is used as the reaction medium. The isomerization proceeds so rapidly that the reaction can be carried out under pressureless conditions and it becomes unnecessary to use pressure-resistant reactors, although the use of pressure has no adverse effects.

The present invention therefore provides a process for the preparation of perfluoropropionyl fluoride (II) by the isomerization of hexafluoropropene oxide (I):

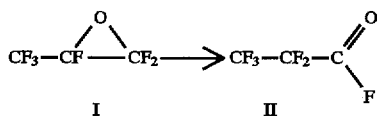

wherein the reaction medium used is a liquid complex ammonium hydrofluoride of the general formula (III):

in which n is an integer or fraction $\leq 3$ and the radicals $R^1$, $R^2$ and $R^3$ are identical or different and each of these radicals is

- an alkyl radical having 1 to 20 carbon atoms, preferably 1 to 12 and especially 1 to 6 carbon atoms,
- a cycloalkyl radical having 5 to 7 carbon atoms,
- an aralkyl radical having 7 to 10 carbon atoms or
- an aryl radical having 6 to 10 carbon atoms which can also be substituted by $C_1$- to $C_3$-alkyl or $C_1$ to $C_3$-alkoxy groups,
- or in which two of the radicals $R^1$ to $R^3$, together with the N atom which carries them, form a 5- to 7-membered ring which can contain an O atom or another N atom,
- or in which the radicals $R^1$ to $R^3$, together with the N atom which carries them, form two or three 5- to 7-membered saturated rings which can contain further N atoms, e.g. in protonated diazabicyclooctane, or in which the radicals $R^1$ to $R^3$ together form a 6-membered heterocyclic ring which can contain one or two N atoms and can also be benzo-fused, e.g. pyridinium, pyrimidinium or quinolinium.

If two of the radicals $R^1$ to $R^3$, together with the N atom which carries them, form a 5- to 7-membered ring, this ring preferably does not contain an O atom or another N atom.

Preferably, at least one of the radicals $R^1$ to $R^3$ is an alkyl radical having 1 to 12 carbon atoms, especially 1 to 6 carbon atoms.

Particularly preferably, all three radicals $R^1$ to $R^3$ are alkyl radicals and have a total of 3 to 12 carbon atoms; very particularly preferably, $R^1=R^2=R^3=CH_3$.

The number n in the general formula (III) is an integer or fraction $\leq 3$, preferably 1.1 to 2.9 and especially 2 to 2.9.

The complex ammonium hydrofluorides can be prepared by reacting the amines directly with HF in the desired molar ratio. The nitrogen atom of the amine is protonated in this reaction; additional HF molecules combine with the fluorine ion to form complex hydrofluoride anions. Some examples of the complex tertiary ammonium hydrofluorides of the general formula (III) which can be used in the process according to the invention are given below:

$(CH_3)_3NH^+H_{1.8}F_{2.8}^-$ $(C_2H_5)_3NH^+H_{1.8}F_{2.8}^-$ $(n-C_3H_7)_3NH^+H_2F_3^-$ $(i-C_3H_7)_2(C_2H_5)NH^+H_{1.6}F_{2.6}^-$ $(n-C_4H_9)_3NH^+H_{1.6}F_{2.6}^-$ $[(CH_3)_2NH-CH_2-]_2^{2+}[H_{1.35}F_{2.35}]_2^{2-}$

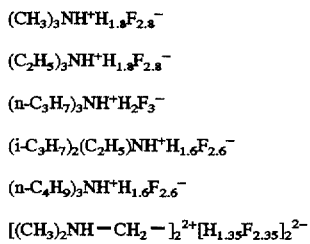

Complex hydrofluorides of this type are known in literature, e.g. from Bull. Soc. Chim. France 1965, pages 1890 to 1892, or from J. Fluorine Chemistry 15 (1980), pages 423 to 434. These are stable complexes with no hydrogen fluoride vapor pressure at all, so they are easy to handle and in some cases can even be distilled in borosilicate glass apparatuses.

The isomerization process according to the invention can be carried out under anhydrous conditions in pressure reactors, e.g. stirred autoclaves, in the manner conventionally used for gaseous/liquid reaction mixtures. However, a pressureless procedure in a bubble column is preferred. The use of bubble columns for suitable gas-liquid reactions is state of the art; the appropriate requirements are known to those skilled in the art.

The temperature is not critical in terms of the isomerization process itself, but rather depends on the properties of the complex tertiary ammonium hydrofluoride (III) used as the reaction medium, i.e. on its freezing point, its temperature-dependent viscosity when using a bubble column, and its decomposition point. The isomerization temperature is generally 0° to 100° C. but preferably 40° to 80° C.

EXAMPLE 1

600 g of the liquid complex ammonium hydrofluoride $[(CH_3)_3NH]^+ [H_{1.8}F_{2.8}]^-$ were introduced as the medium, up to a height of 160 cm, into an externally heated glass tube of length 2 m and internal diameter 25 mm, which was equipped as a bubble column and lined with a transparent tetrafluoroethylene/hexafluoropropene copolymer (FEP), and were heated to 60° C. Hexafluoropropene oxide was then introduced at the foot of the bubble column and finely dispersed in the medium. The product gas emerging at the head of the bubble column was condensed in a trap cooled with dry ice/methanol. The condensate was examined by $^{19}F$ NMR spectroscopy. A conversion of 95 mol % was determined on the basis of the amount of hexafluoropropene oxide used; the yield of perfluoropropionyl fluoride was 97.9 mol % on the basis of this conversion.

EXAMPLE 2

The reaction described in Example 1 was repeated except that the temperature was only 30° C. Because the viscosity of the medium was now higher, the throughput applied to the bubble column was lower than in Example 1; the residence time of the gas in the medium was correspondingly longer. According to NMR analysis of the product gas, the conversion was 95.9 mol % on the basis of the amount of hexafluoropropene oxide used; on the other hand, the yield of perfluoropropionyl fluoride on the basis of this conversion was practically 100 mol %.

EXAMPLE 3

The reaction described in Example 1 was repeated except that the bubble column was kept at a temperature of 80° C. According to NMR analysis of the product gas, the conversion was 88 mol % on the basis of the amount of hexafluoropropene oxide used; the yield of perfluoropropionyl fluoride on the basis of this conversion was 98 mol %.

EXAMPLE 4

520 g of the liquid complex ammonium hydrofluoride $[(n-C_4H_9)_3NH]^+ [H_{1.1}F_{2.1}]^-$ were introduced to a height of 150 cm into the bubble column described in Example 1, and were heated to 60° C. The introduction of hexafluoropropene oxide and the analysis were then performed as described in Example 1. The conversion of the hexafluoropropene oxide used was 100 mol %; the product gas contained 96 mol % of perfluoropropionyl fluoride.

EXAMPLE 5

The reaction described in Example 4 was carried out at a temperature of 70° C. According to NMR analysis, the conversion of the hexafluoropropene oxide used was again 100 mol %; the product gas contained 99 mol % of perfluoropropionyl fluoride.

EXAMPLE 6

100 g of the liquid complex ammonium hydrofluoride

were placed in a stirred autoclave of 300 ml capacity (material: ®Hastelloy C) and about 20 g of hexafluoropropene oxide were introduced under pressure from a pressurized storage bottle. The reaction mixture was subsequently heated at 60° C. for 2 h under autogenous pressure, with stirring, and the pressure was then released via a cooling trap in a dry ice bath. According to $^{19}F$ NMR analysis, the gas mixture contained perfluoropropionyl fluoride in a concentration of 97.3 mol %, together with 2.6 mol % of unreacted hexafluoropropene oxide. No dimerization or oligomerization products of hexafluoropropene were detectable either in the contents of the cold trap or in the hydrofluoride residue remaining in the autoclave.

We claim:

1. A process for the preparation of perfluoropropionyl fluoride (II) by the isomerization of hexafluoropropene oxide (I):

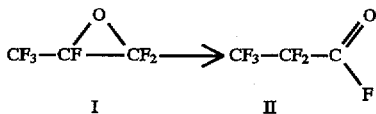

wherein the reaction medium used is a liquid complex ammonium hydrofluoride of the general formula (III):

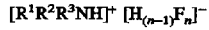     III in which n is an integer or fraction $\leq 3$ and the radicals $R^1$, $R^2$ and $R^3$ are identical or different and each of these radicals is an alkyl radical having 1 to 20 carbon atoms,
a cycloalkyl radical having 5 to 7 carbon atoms,
an aralkyl radical having 7 to 10 carbon atoms or
an aryl radical having 6 to 10 carbon atoms which can also be substituted by $C_1$- to $C_3$-alkyl or $C_1$ to $C_3$-alkoxy groups, or in which two of the radicals $R^1$ to $R^3$, together with the N atom which carries them, form a 5- to 7-membered ring which can contain an O atom or another N atom, or in which the radicals $R^1$ to $R^3$, together with the N atom which carries them, form two or three 5- to 7-membered saturated rings which can contain further N atoms, or in which the radicals $R^1$ to $R^3$ together form a 6-membered heterocyclic ring which can contain one or two N atoms and can also be benzo-fused.

2. The process as claimed in claim 1, wherein an ammonium hydrofluoride of the formula (III) is used in which at least one of the radicals $R^1$ to $R^3$ is an alkyl radical having 1 to 12 carbon atoms.

3. The process as claimed in claim 1, wherein an ammonium hydrofluoride of the formula (III) is used in which at least one of the radicals $R^1$ to $R^3$ is an alkyl radical having 1 to 6 carbon atoms.

4. The process as claimed in claim 1, wherein an ammonium hydrofluoride of the formula (III) is used in which all three radicals $R^1$ to $R^3$ are alkyl radicals and have a total of 3 to 12 carbon atoms.

5. The process as claimed in claim 1, wherein an ammonium hydrofluoride of the formula (III) is used in which $R^1=R^2=R^3=CH_3$.

6. The process as claimed in claim 1, wherein an ammonium hydrofluoride of the formula (III) is used in which n is an integer or fraction from 1.1 to 2.9.

7. The process as claimed in claim 1, wherein an ammonium hydrofluoride of the formula (III) is used in which n is an integer or fraction from 2 to 2.9.

8. The process as claimed in claim 1, wherein two of the radicals $R^1$ to $R^3$, together with the N atom which carries them form a 5 to 7-membered ring, in which said ring does not contain an O atom or another N atom.

9. The process as claimed in claim 7, wherein $R^1$ to $R^3$ is an alkyl radical having 1 to 6 carbons.

10. The process as claimed in claim 9, wherein all three radicals $R^1$ to $R^3$ are alkyl radicals and have a total of 3 to 12 carbon atoms.

* * * * *